US00PP29716P2

(12) United States Plant Patent
de Ruyver

(10) Patent No.: US PP29,716 P2
(45) Date of Patent: Sep. 25, 2018

(54) ***FELICIA* PLANT NAMED 'RUYFEM1702'**

(50) Latin Name: ***Felicia* hybrid**
Varietal Denomination: RUYFEM1702

(71) Applicant: Kurt de Ruyver, Oudenaarde (BE)

(72) Inventor: Kurt de Ruyver, Oudenaarde (BE)

( * ) Notice: Subject to any disclaimer, the term of this patent is extended or adjusted under 35 U.S.C. 154(b) by 0 days.

(21) Appl. No.: 15/731,658

(22) Filed: Jul. 13, 2017

(51) Int. Cl.
*A01H 5/02* (2018.01)

(52) U.S. Cl.
USPC ..... Plt./430

(58) Field of Classification Search
USPC ..... Plt./430
See application file for complete search history.

*Primary Examiner* — Susan McCormick Ewoldt
(74) *Attorney, Agent, or Firm* — Samuel R. McCoy, Jr.

(57) ABSTRACT

'RUYFEM1702' is a new and distinctive variety of *Felicia* which is characterized by a broad upright to spreading growth habit with inflorescence carried within and above the foliage, very large capitula inflorescences with dark yellow disc florets and prominent white ray florets, and day-neutral flowering habit with a long natural flowering season. The new variety propagates successfully by stem cuttings and has shown to be uniform and stable in the resulting generations from asexual propagation.

3 Drawing Sheets

Latin name of the genus and species: The Latin name of the genus and species of the novel variety disclosed herein is *Felicia* hybrid.

Variety denomination: The inventive variety of *Felicia* hybrid disclosed herein has been given the variety denomination 'RUYFEM1702'.

BACKGROUND OF THE INVENTION

Parentage: 'RUYFEM1702' is the result of a controlled cross-pollination breeding program carried out by the inventor at a commercial nursery in Oudenaarde, Belgium, in August of 2015. The inventor performed a controlled cross-pollination of the seed parent, *Felicia amelloides* 'Alba' (not patented), with an unnamed *Felicia hyssopifolia* seedling pollen parent (not patented). Seed from said cross was harvested, then germinated, and the resulting 80 seedlings were grown to a mature size in order to evaluate for desirable commercial characteristics. Five candidate plants which exhibited unique characteristics were initially isolated and, after further evaluation, the number of candidates was reduced to two. In May of 2016, the inventor selected the new *Felicia* cultivar from the remaining two candidates due to its large flowers and unique bloom habit. This new and distinctive cultivar was given the name 'RUYFEM1702'.

Asexual Reproduction: Asexual reproduction of 'RUYFEM1702' was first accomplished in November of 2016 by rooting softwood stem cuttings at a commercial greenhouse in Heythuysen, the Netherlands. Two successive generations have shown that the unique features of the instant cultivar are stable and reproduce true to type.

SUMMARY OF THE INVENTION

The cultivar 'RUYFEM1702' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Felicia* cultivar, 'RUYFEM1702'.

1. *Felicia* 'RUYFEM1702' exhibits a broad upright to spreading growth habit with inflorescence carried within and above the foliage; and
2. *Felicia* 'RUYFEM1702' exhibits very large capitula with dark yellow disc florets and prominent white ray florets in a single whorl around the receptacle; and
3. *Felicia* 'RUYFEM1702' exhibits ray florets with an aspect which can vary, from one flower to the next, from flat to slightly carinate and an attitude which can vary from flat to curved upward to reflexed, giving the flowers a whimsical appearance; and
4. *Felicia* 'RUYFEM1702' is day-neutral and exhibits a long natural flowering season and flowers which remain open, even under cloudy conditions.

BOTANICAL DESCRIPTION OF THE PLANT

Figure 1:
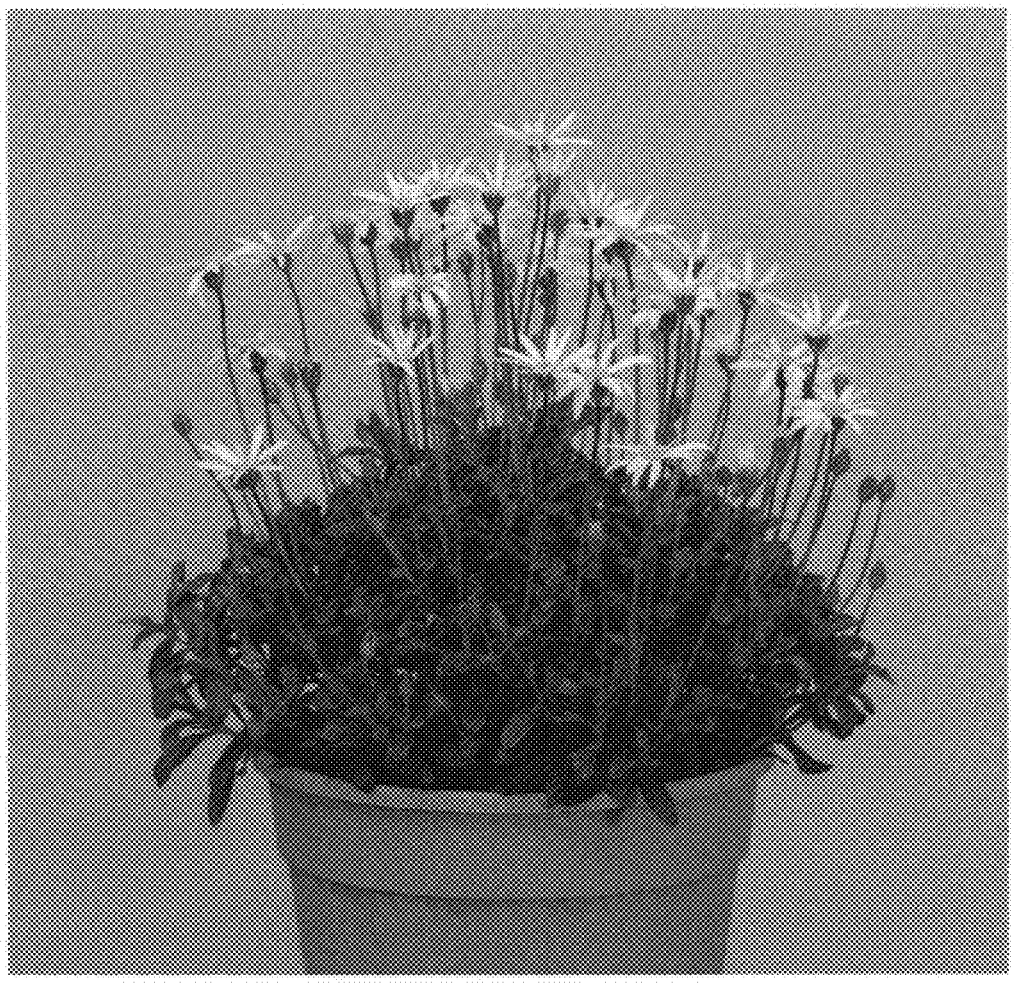
FIG. 1 shows, as nearly true as it is reasonably possible to make the same in color illustrations of this type, an exemplary 'RUYFEM1702' plant at approximately 10 week old, potted into an 18 cm nursery pot, grown in a greenhouse in Oudenaarde, Belgium. The highly variable aspect and attitude of the ray florets, from one flower to the next, can be seen in the figure.
Figure 2:
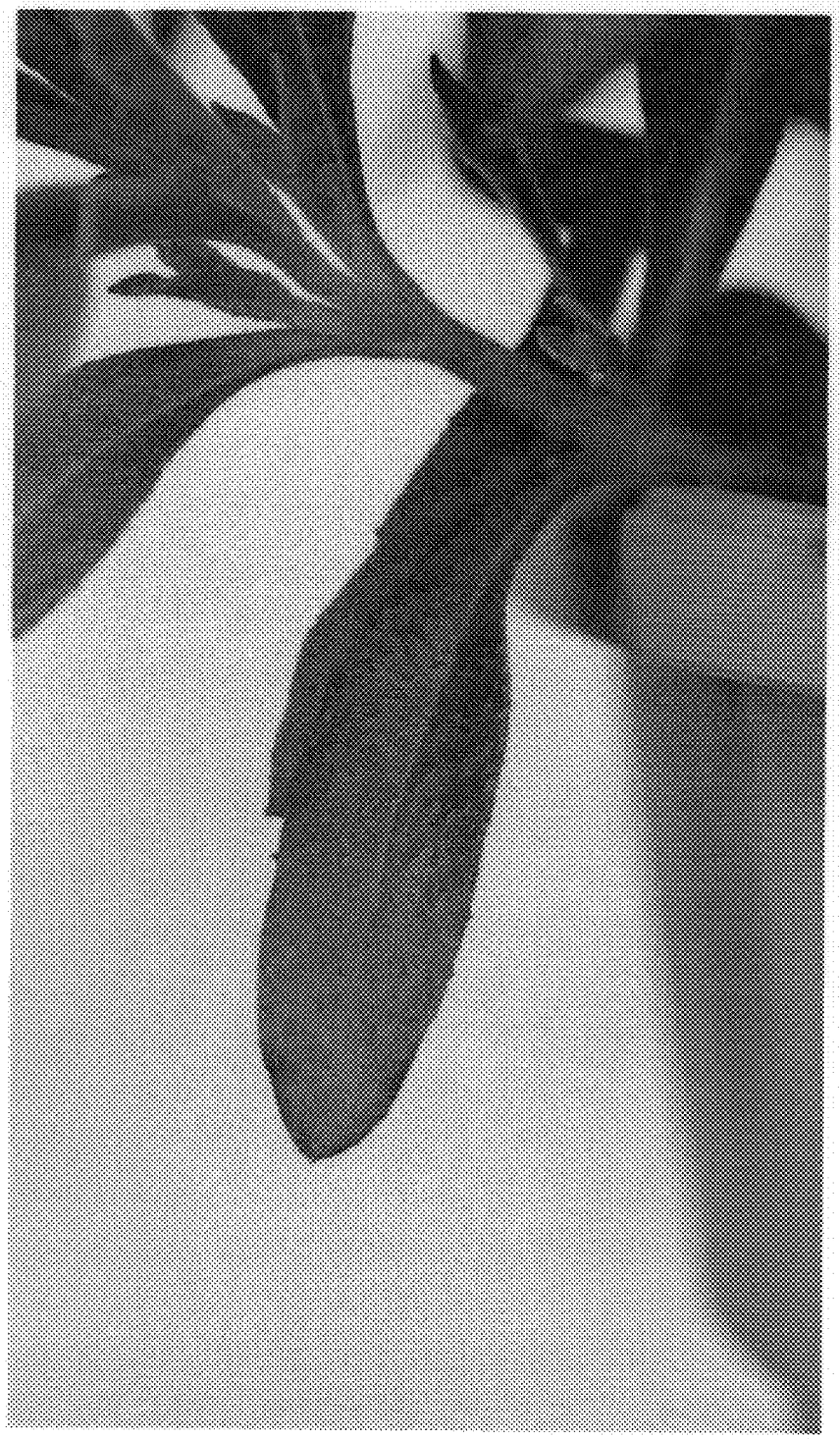
FIG. 2 shows, as nearly true as it is reasonably possible to make the same in color illustrations of this type, the typical foliage of the plant in FIG. 1.
Figure 3:
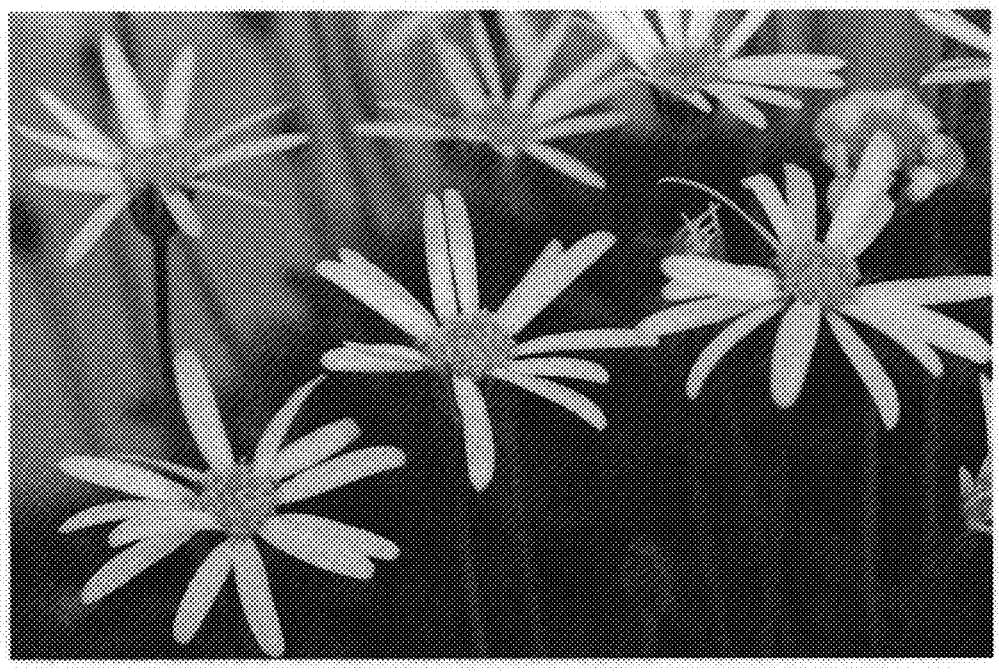
FIG. 3 shows, as nearly true as it is reasonably possible to make the same in color illustrations of this type, the typical flowers of the plant in FIG. 1.

The following is a detailed botanical description of a new and distinct variety of *Felicia* known as 'RUYFEM1702', based upon observations of 10 week old greenhouse-grown plants in 18 cm nursery containers, grown in Oudenaarde, Belgium. Plants were grown using conventional greenhouse production protocols for *Felicia* plants which consisted of both regular overhead irrigation and flood bench irrigation, as well as fertigation applications. Pest or disease control measures were utilized in production as required. Plants were produced with full sun exposure and no photoperiodic treatments or artificial light was given to the plants. Observation data was recorded in June of 2017.

Those skilled in the art will appreciate that certain characteristics will vary with older or, conversely, with younger plants. 'RUYFEM1702' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 edition.

A botanical description of 'RUYFEM1702' and comparisons with the parents and most similar variety of common knowledge are provided below.

General plant description:

*Growth habit*.—A broad, upright to spreading herbaceous perennial with inflorescence carried within and above the foliage.

*Plant form*.—Flattened globular to broad obovate.

*Height*.—14.5 cm to the top of the foliar plane; 24.3 cm to the top of the floral plane.

*Spread*.—30.0 cm.

*Plant vigor*.—Moderate.

*Growth rate*.—Moderate.

*Propagation*.—Softwood stem cuttings; rooting is initiated in approximately 10 days when grown in a greenhouse with an ambient average temperature of 18 degrees Celsius.

*Time to produce a finished plant*.—Approximately 12 weeks are required to produce a marketable finished plant in a 9 cm pot.

*Pest resistance and susceptibility*.—Not any more or less tolerant or susceptible to pests or diseases known to effect *Felicia*.

*Environmental tolerances*.—Adapt to, at least, USDA Zones 9 to 11 and temperatures ranging from minus 2 degrees Celsius to 35 degrees Celsius; moderate tolerance to rain; moderate tolerance to wind.

Root system: Thin, fibrous, and freely branched.

Stem:

*Branching habit*.—Basally branching main stem; freely branching with lateral branches.

*Number of primary (main) stems per plant*.—10.

*Number of secondary (lateral) branches per plant*.—7.

*Appearance and shape*.—Rounded.

*Lateral branch length*.—5.9 cm.

*Lateral branch diameter*.—0.2 cm.

*Internode length*.—1.8 cm.

*Luster*.—Very slightly glossy.

*Aspect*.—Main stems are an average angle of 50 degrees from vertical; stems vary from between 10 to 90 degrees from vertical. Lateral branches are at an average angle of 30 degrees to the main stems.

*Strength*.—Moderately strong.

*Color, juvenile*.—Yellow-green, nearest RHS 144B.

*Color, mature*.—Yellow-green, nearest to in between RHS 144A and 144B.

*Color at internodes*.—Yellow-green, nearest to in between RHS 144A and 144B.

*Pubescence*.—Densely pubescent; very short, strigose hairs with an average length of 0.05 cm and colored green-white, RHS 157D.

*Stem luster*.—Slightly glossy.

Foliage:

*Arrangement*.—Opposite.

*Attachment*.—Sessile.

*Division*.—Simple.

*Abundance*.—Very abundant.

*Lamina*.—Dimensions — 4.0 cm long and 1.2 cm wide, on average. Shape — Obovate. Aspect — Flat to very slightly carinate. Apex — Obtuse to acute. Base — Long attenuate. Margin — Entire to very shallowly toothed with one or two teeth on each side of the leaf blade; not undulated. Pubescence, texture and luster of adaxial surface — Densely pubescent, rough to the touch, and slightly glossy. Pubescence, texture and luster of abaxial surface — Densely pubescent, rough to the touch, and very slightly glossy. Color — Juvenile foliage, adaxial surface — Green, nearest to RHS 143A. Juvenile foliage, abaxial surface — Green, nearest to in between RHS 143B and 143C. Mature foliage, adaxial surface — In between green, nearest to RHS NN137B, and yellow-green, nearest to RHS 147A. Mature foliage, abaxial surface — Yellow-green, nearest to RHS 146B. Venation — Pattern — Pinnate. Venation color, adaxial surface — Yellow-green, nearest to RHS 144A. Venation color, abaxial surface — Yellow-green, nearest to RHS 146B.

*Petiole*.—None; leaves are sessile.

Inflorescence:

*Type*.—Terminal capitula comprised of a receptacle, disc florets, and ray florets.

*Natural flowering season*.—Late spring into summer in Oudenaarde, Belgium.

*Flowering habit*.—Very freely flowering; day-neutral.

*Dimensions*.—1.6 cm high, not including peduncle, and 3.7 cm in diameter.

*Quantity of inflorescence per plant*.—70, on average.

*Quantity of flowers per inflorescence*.—80, on average.

*Attitude*.—Upright.

*Peduncles*.—Length — Average of 11.3 cm. Diameter — Average of 0.15 cm. Attitude — Upright; at the same angle as the lateral branch. Strength — Strong. Texture — Densely pubescent; short, strigose hairs with an average length of 0.04 cm and colored green-white, RHS 157D. Luster — Moderately glossy. Color — Yellow-green, nearest to RHS 144A, and darker and more yellow towards the distal end, nearest to RHS 148A.

Flower buds:

*Shape*.—Ovate.

*Length*.—Average of 1.0 cm.

*Diameter*.—Average of 0.6 cm.

*Texture*.—Moderately pubescent; very short, strigose hairs with an average length of 0.04 cm and colored green-white, RHS 157D.

*Luster*.—Matte.

*Color*.—Yellow-green, nearest to in between RHS 145A and 145B; longitudinally striped with green, nearest to RHS 137B; apex is green, RHS 137B.

Flower:

*Flower type*.—Composite; capitula.

*Fragrance*.—None.

*Flower longevity*.—10 days, on average.

*Persistence*.—Persistent.

*Disc diameter*.—0.9 cm.

*Receptacle shape*.—Inverted triangular.

*Receptacle height*.—0.2 cm.

*Receptacle diameter*.—0.3 cm.

*Receptacle color*.—Yellow-green, nearest to RHS 138C.

*Ray florets*.—Quantity of florets per capitula — 14. Shape — Oblanceolate. Arrangement — Rotate around disc; florets are unfused. Attitude — Outward, with an average angle of 15 degrees to horizontal. Aspect — Slightly carinate; slightly reflexed. Dimensions — 2.1 cm long and 0.35 cm wide. Apex — Undeeply finely praemorse. Base — Attenuate. Margin — Entire; not undulated. Texture and luster, upper surface — Glabrous, velvety and matte. Texture and luster, lower surface — Glabrous, velvety and slightly glossy. Color, when opening, upper surface — White, nearest to NN155C. Color, when opening, lower surface — White, nearest to NN155C. Color, when fully opened, upper surface — White, nearest to NN155C. Color, when fully opened, lower surface — White, nearest to NN155C. Venation, when fully opened, upper surface — White, nearest to NN155C. Venation, when fully opened, lower surface — White, nearest to NN155C.

*Disc florets*.—Quantity of florets per capitula — 75. Shape — Tubular. Around each disc floret is a single whorl of soft hairs with an average length of 0.4 cm and colored green-white, nearest to RHS 157D. Arrangement — Radial symmetry; five whorl; florets are fused with only 10 to 15 percent of the distal portion of the floret being free. Attitude — Upright. Length — 0.9 cm. Width — 0.2 cm. Apex of the floret lobe — Acute. Base — Fused into a tube. Margin of the free floret lobe — Entire; not undulated. Texture and luster, upper surface — Smooth, glabrous and slightly glossy. Texture and luster, lower surface — Smooth, glabrous and slightly glossy. Color, when opening, upper surface — Apex is yellow, nearest to in between RHS 4A and 4B; mid-section and base are green-white, in between RHS 155C and 157D. Color, when opening, lower surface — Apex is yellow, nearest to in between RHS 4A and 4B; mid-section and base are green-white, in between RHS 155C and 157D. Color, when fully opened, upper surface — Apex is yellow, nearest to RHS 5B; mid-section and base are green-white, RHS 157D. Color, when fully opened, lower surface — Apex is yellow, nearest to RHS 5B; mid-section and base are green-white, RHS 157D. Faded color, upper surface — Apex is yellow, nearest to RHS 13A; mid-section and base are green-white, RHS 157C. Faded color, lower surface — Apex is yellow, nearest to RHS 13A; mid-section and base are green-white, RHS 157C. Venation — No visible venation.

*Involucre; phyllaries*.—Arrangement — Rotate; free; one whorl around the disc. Quantity — 12. Length — 1.0 cm. Width — 0.15 cm. Shape — Lanceolate to narrow oblanceolate. Apex — Acute. Base — Cuneate. Margin — Entire. Texture, upper surface — Glabrous. Texture, lower surface — Moderately pubescent; very short, strigose hairs with an average length of 0.04 cm and colored green-white, RHS 157D. Luster, upper surface — Moderately glossy. Luster, lower surface — Matte. Color, fully opened, upper surface — Green, nearest to RHS 138A; proximal half is lighter, nearest to RHS 138A; margins are a translucent green-white, nearest to RHS 157D. Color, fully opened, lower surface — Green, nearest to RHS 143B; margins are a translucent green-white, nearest to RHS 157D.

Reproductive organs:

*Stamens*.—Quantity — 5 per disc floret; none present on ray florets. Anthers — Shape — Narrow oblong. Dimensions — Approximately 0.2 cm long and 0.2 cm wide. Color — Yellow, nearest to RHS 7A. Filaments — Length — 0.3 cm, on average. Color — White, nearest to in between RHS NN155C and NN155D. Pollen, amount — Moderately abundant. Pollen color — Yellow, nearest to in between RHS 10A and 10B.

*Pistil*.—Quantity — 1 pistil for each disc floret; no pistils present on ray florets. Length — 0.7 cm. Style — Length — 0.65 cm. Color — White, nearest to RHS NN155D, and fading to yellow towards the distal end, nearest to RHS 7B. Stigma — Shape — Cleft; decurrent. Diameter — 0.1 cm. Color — Yellow, nearest to RHS 7A. Ovary Color — Green-white, RHS 157D.

Seed and fruit: No fruit or seeds have been detected to date.

COMPARISONS WITH THE PARENT PLANTS AND MOST SIMILAR VARIETY OF COMMON KNOWLEDGE

Plants of the new cultivar 'RUYFEM1702' differ from its seed parent, *Felicia amelloides* 'Alba' (not patented), by the characteristics described in Chart 1.

CHART 1

| Characteristic | 'RUYFEM1702' | 'Alba' |
|---|---|---|
| Flower size. | Approximately twice the size of the seed parent. | Approximately half the size of 'RUYFEM1702'. |
| Flowering habit. | Day-neutral; flowers year long, | Not day-neutral; does not flower year long. |

Plants of the new cultivar 'RUYFEM1702' differ from its pollen parent, an unnamed *Felicia hyssopifolia* seedling, by the characteristics described in Chart 2.

CHART 2

| Characteristic | 'RUYFEM1702' | The pollen parent |
|---|---|---|
| Flower size. | Approximately twice the size of the pollen parent. | Approximately half the size of 'RUYFEM1702'. |
| Flowering habit. | Day-neutral; flowers year long, | Not day-neutral; does not flower year long. |

Plants of the new cultivar 'RUYFEM1702' may be distinguished from its most similar known commercial comparator, *Felicia amelloides* 'Felicitara Blue', by the characteristics described in Chart 3.

CHART 3

| Characteristic | 'RUYFEM1702' | 'Felicitara Blue' |
|---|---|---|
| Flower size. | Larger than those of 'Felicitara Blue'. | Smaller than those of 'RUYFEM1702'. |

CHART 3-continued

| Characteristic | 'RUYFEM1702' | 'Felicitara Blue' |
|---|---|---|
| General coloration of the flowers. | Blue flowers. | White flowers. |

That which is claimed is:

1. A new and distinct variety of *Felicia* hybrid plant named 'RUYFEM1702', substantially as described and illustrated herein.

* * * * *